United States Patent [19]

Ulman

[11] Patent Number: 5,665,396
[45] Date of Patent: Sep. 9, 1997

[54] APPARATUS FOR MAKING THREE-DIMENSIONAL FABRICS

[75] Inventor: John Thomas Ulman, Woodbridge, N.J.

[73] Assignee: McNeil-PPC, Inc., Skillman, N.J.

[21] Appl. No.: 446,262

[22] Filed: May 22, 1995

Related U.S. Application Data

[62] Division of Ser. No. 999,328, Dec. 31, 1992, Pat. No. 5,540,872.

[51] Int. Cl.⁶ .............................. D04H 01/72; B27N 5/00
[52] U.S. Cl. .................... 425/80.1; 156/62.2; 425/388
[58] Field of Search ..................... 425/82.1, 80.1, 425/388; 264/115, 121; 156/62.2, 62.4

[56] References Cited

U.S. PATENT DOCUMENTS

| | | | |
|---|---|---|---|
| 2,986,780 | 6/1961 | Bletzinger | 425/82.1 |
| 3,939,240 | 2/1976 | Savich | 264/121 |
| 4,016,628 | 4/1977 | Kolbach | 425/82.1 |
| 4,103,058 | 7/1978 | Humlicek | 156/62.4 |
| 4,666,647 | 5/1987 | Enloe et al. | 425/80.1 |
| 5,004,579 | 4/1991 | Wislinski et al. | 425/82.1 |
| 5,064,484 | 11/1991 | Craig et al. | 264/121 |
| 5,229,052 | 7/1993 | Billiu | 425/82.1 |

FOREIGN PATENT DOCUMENTS 566851  5/1958  Belgium .................... 264/115

Primary Examiner—Robert Davis
Attorney, Agent, or Firm—James P. Barr

[57] ABSTRACT

A method of manufacturing a three-dimensional fabric of the type which may be used in absorbent garments, dressings or the like involves the use of an apertured collector element which has a predetermined three-dimensional shape. The method involves positioning material adjacent to one side of the apertured collector element and developing a pressure differential between the one side of the apertured collector element and a second, opposite side to force the fabric material against the apertured collector element. The material, which has conformed to the shape of the collector element, is then solidified into its intended three-dimensional shape.

6 Claims, 4 Drawing Sheets

APPARATUS FOR MAKING THREE-DIMENSIONAL FABRICS

This is a division of application Ser. No. 07/999,328, Dec. 31, 1992 and now U.S. Pat. No. 5,540,872, which is hereby incorporated by reference.

BACKGROUND OF THE INVENTION

1. Field of the Invention

This invention relates to a system and a method for fabricating three-dimensional fabrics for use in sanitary napkins, incontinence pads, surgical dressings or the like. More specifically, the invention relates to forming three-dimensional surfaces such as flexible projections, ridges, wells or the like which may be used to direct fluid within a product, or to provide improved anatomical fit.

2. Description of the Prior Art

Products such as sanitary napkins, incontinence pads and surgical dressings often include a layer of absorbent material, and a backing layer or moisture barrier which is impervious to fluid. The absorbent material includes a surface for contacting the body of the consumer or patient, so that body fluids are absorbed into the product and are contained by the moisture barrier. In the case of sanitary napkins and incontinence pads, an adhesive strip may be provided on an outer surface of the moisture barrier for temporarily securing the product to an undergarment of the consumer.

Conventionally, the body contacting surface of the absorbent material in such a product is substantially flat and uniform. Attempts have been made to texture the body-contacting surface by embossing, but embossing tends to compress the absorbent material and lesson its moisture absorbing characteristics. While the potential advantages of a textured body contacting surface, such as greater absorbent surface area and improved anatomical fit are generally recognized, the disadvantages which are inherent in compression type forming techniques such as embossing have, precluded any successful introduction of a textured absorbent product into the marketplace.

It is clear that there has existed a long and unfilled need in the prior art for a system and method for making a three-dimensional, textured absorbent fabric which does not have diminished moisture absorbing characteristics with respect to conventional, non-textured absorbent products.

SUMMARY OF THE INVENTION

Accordingly, it is an object of the invention to provide an improved method for manufacturing an absorbent, three-dimensional fabric which exhibits improved moisture absorbency characteristics with respect to conventional non-textured absorbent products.

It is further an object of the invention to provide a system for making a three-dimensional, absorbent fabric which exhibits such improved moisture absorbing characteristics.

In order to achieve the above and other objects of the invention, a method of manufacturing a three-dimensional fabric of the type which may be used in absorbent garments, dressings or the like includes, according to a first aspect of the invention, steps of (a) providing an apertured collector element having a predetermined three-dimensional shape; (b) positioning material to adjacent to one side of the apertured collector element; (c) developing a pressure differential between the one side of the apertured collector element and a second, opposite side to force the fabric material against one side of the apertured collector element so that the material conforms to the predetermined three-dimensional shape; and (d) solidifying the so-conformed material into the three-dimensional shape.

According to a second aspect of the invention, a method of manufacturing a three-dimensional fabric of the type which may be used in absorbent garments, dressings or the like includes steps of (a) providing an apertured collector element having a predetermined three-dimensional shape; (b) positioning a web material adjacent to one side of the apertured collector element; (c) positioning fibrous fill material adjacent to the web material; and (d) solidifying the web and the fibrous film material into the three-dimensional shape.

According to a third aspect of the invention, a system for manufacturing a three-dimensional fabric of the type which may be used in absorbent garments, dressings or the like includes an apertured collector element having a predetermined three-dimensional shape; structure for positioning material adjacent to one side of the apertured collector element; structure for developing a pressure differential between the one side of the apertured collector element and a second, opposite side to force the fabric material against the one side of the apertured collector element so that the material conforms to the predetermined three-dimensional shape; and structure for solidifying the so conformed material into the three-dimensional shape.

According to a fourth aspect of the invention, a system for manufacturing a three-dimensional fabric of the type which may be used in absorbent garments, dressings or the like includes an apertured collector element having a predetermined three-dimensional shape; structure for positioning a web of material adjacent to one side of the apertured collector element; structure for positioning fibrous film material adjacent to the web of material; and structure for solidifying the web and the fibrous film material into the three-dimensional shape.

These and various other advantages and features of novelty which characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENT(S)

Figure 1:
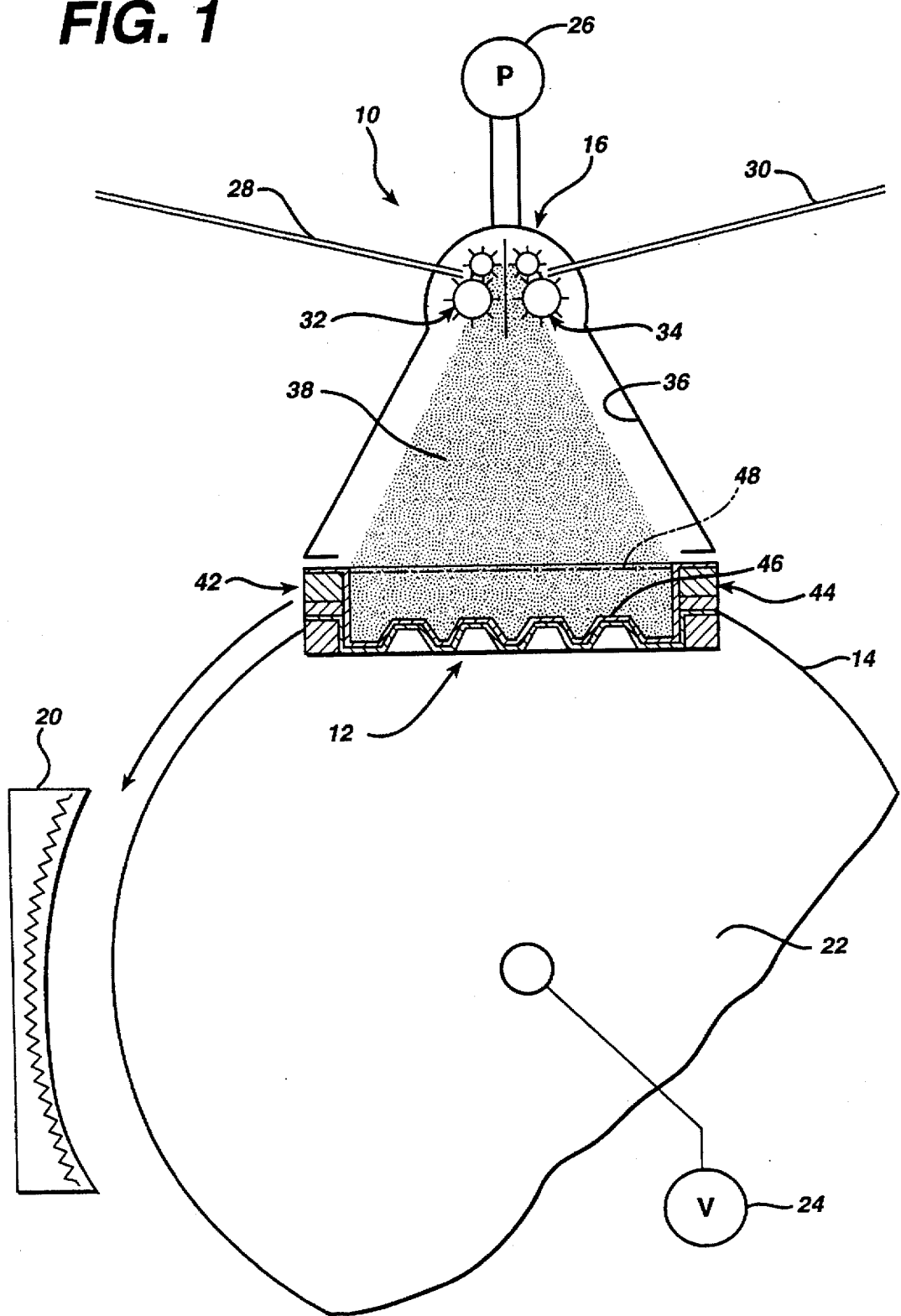
FIG. 1 is a diagrammatical view of a system for manufacturing a three-dimensional fabric according to a preferred embodiment of the invention.

Referring now to the drawings, wherein like reference numerals designate corresponding structure throughout the views, and referring in particular to FIG. 1, a system 10 for manufacturing a three-dimensional fabric of the type which may be used in absorbent garments, dressings or the like includes a shaping assembly 12 which is mounted on a rotary conveyer 14 for movement between a fill station 16 and a heating station 18 having a heater 20. As is further shown in FIG. 1, rotary conveyer 14 includes an internal chamber 22 which is in communication with a source 24 of vacuum. Fill station 16 includes a hood-like structure 36 defining a pressurized chamber 38 which is connected to a pressure source 26, shown at the top of FIG. 1.

Referring again to FIG. 1, a source of fiber 28 is fed into a first cutter 32 contained within hood-like structure 36. Similarly, a source of pulp 30 is fed into a second cutter 34, also contained within hood-like structure 36. Cutters 32, 34 are designed to cut fiber 28 and pulp 30, respectively, into small pieces, which are mixed within hood-like structure 36 by their momentum and by airflow from pressure source 26 to settle within shaping assembly 12, as will be described in greater detail below.

Figure 2:
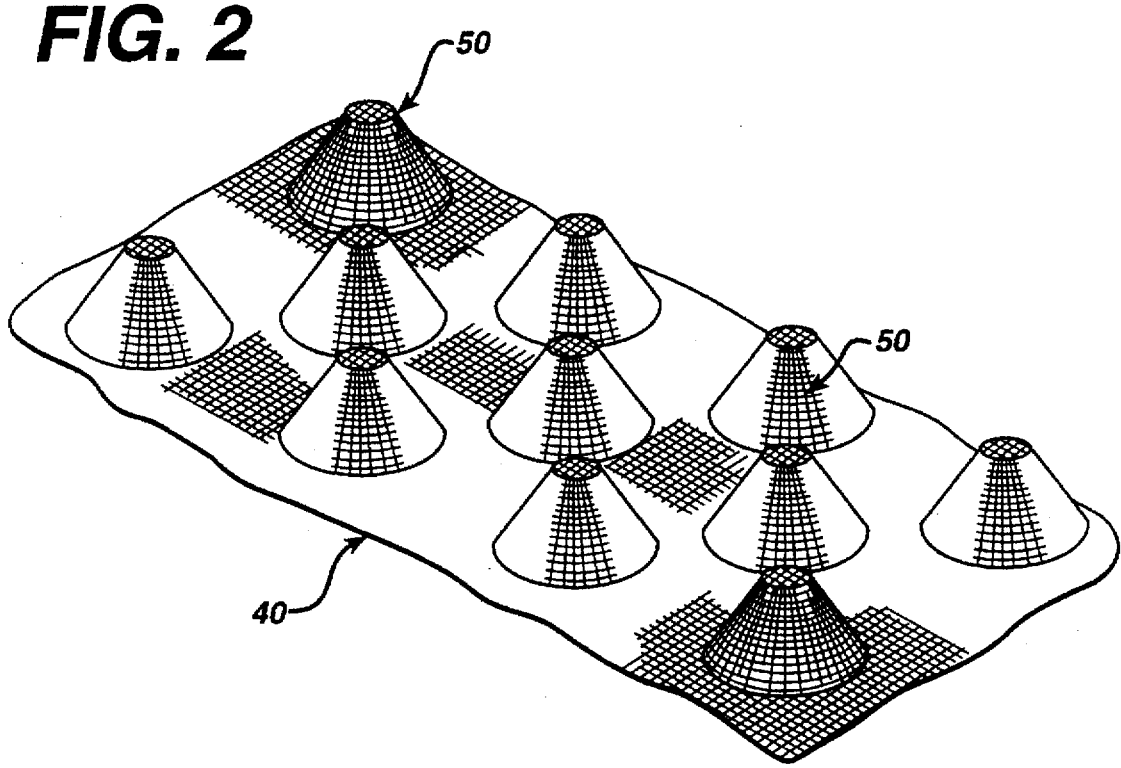
FIG. 2 is a fragmentary perspective view of a contoured screen which is used in the system depicted in FIG. 1.

Looking now to FIGS. 1 and 2, shaping assembly 12 includes a contoured screen 40 which is mounted between a pair of oppositely facing mounting blocks 42, 44. In the preferred embodiment of the invention, as may be seen in FIG. 2, contoured screen 40 is formed so as to have a pattern of spaced projections 50 formed thereon which are shaped as truncated cones. It is to be understood, however, that the exact shape of contoured screen 40 will vary according to the specific contour that is desired for the three-dimensional fabric being manufactured.

According the preferred embodiment of the invention, a cover 46 of air permeable material is positioned over the surface of contoured screen 40 which faces toward pressure source 26. The pressure differential between pressurized chamber 38 and internal chamber 22 induced by pressure source 26 and vacuum source 24 will cause cover 46 to conform to the surface of contoured screen 40, as shown in FIG. 1.

During operation of the system 10, the fragments of fiber 28 and pulp 30 will settle on top of the cover 46 which has assumed the shape of contoured screen 40, until a fill level 48 is reached. At this point, fill station 16 momentarily stops, and rotary conveyer 14 transport shaping assembly 12 to a position which is adjacent to heating station 18. At that point, heat from heater 20 will melt a thermoplastic component of the fiber 28, thereby binding the fibers 28 to the fibers from pulp 30, and to the cover 46. Shaping assembly 12 is then permitted to cool, so that fibers 28, pulp 30 and cover 46 will solidify into a completed absorbent three-dimensional fabric.

Alternatively, the solidification process could be performed by blowing heated air through shaping assembly 12 at fill station 14 rather than at a separate heating station.

Pulp 30 may be substantially any type of absorbent pulp, such as wood fiber pulp. Most preferably, pulp 30 is Supersoft brand ELM pulp fiber, which is commercially obtainable from the International Paper Co. Fiber 28 can be any basic fiber that has a surface melt point (as in the case of a bico fiber) or melt point range (as in the case of a staple fiber) of 110° C. to 150° C. The fibers 28 can be a bico, staple or adhesive fiber. A bico fiber would have a core with a higher melt point than its sheath, or two coextruded portions having different melting temperatures. Staple and adhesive fibers would have a melting point less than the temperature at which pulp 30 would begin to degrade or "yellow." Examples of commercially obtainable materials which could be used as the fiber 28 include Celbond brand #K54 polyester/copolyester fiber which is available from Hoechst Celanese Corporation, Celbond brand #255 fiber also available from Hoechst Celanese Corporation, DuPont binder fiber #D262 polyester/copolyester fiber, DuPont binder fiber #D270 polyester/copolyester fiber and adhesive fiber #410, which is available from the Eastman Chemical Company.

Cover 46 could be any type of material through which air can be forced, such as a woven cloth, a non-woven fabric, an unbonded non-woven fabric, or a perforated plastic material. Most preferably, cover 46 is fabricated from a fusible fiber non-woven fabric such as made from ENKA brand #1050, #1070 or #1045 fusible fiber, which are available from Johnson and Johnson Worldwide Absorbent Products, or a blend of Hollofil pulp and ENKA fibers which is available under the brand TDS from Johnson and Johnson Worldwide Absorbent Products.

It is to be understood that a three-dimensional fabric according to the invention could be manufactured by using cover 46 without fiber 28 or pulp 30. Alternatively, a three-dimensional fabric could be manufactured according to the invention by using fiber 28 without pulp 30 or cover 46, or with fiber 28 and cover 46 without the use of pulp 30.

In order to enhance the ability of cover 46 to conform to the textured surface of contoured screen 40, cover 46 may be crimped prior to its placement adjacent to contoured screen 40.

Figure 3:
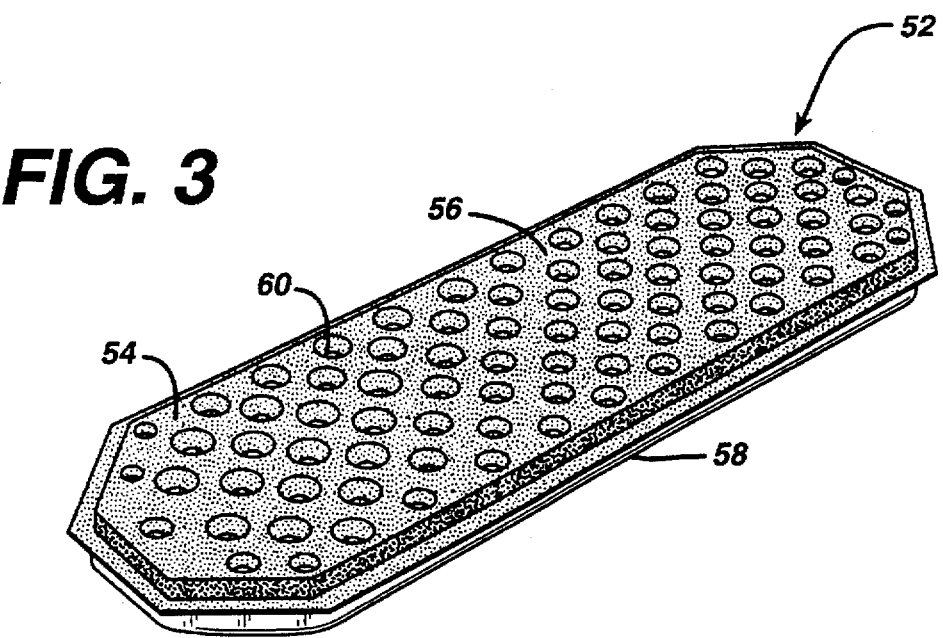
FIG. 3 is a perspective view of an absorbent product which has been fabricated by the system depicted in FIGS. 1 and 2.

FIG. 3 depicts an absorbent product 52, in this case a sanitary napkin, having a contoured absorbent surface 56 which has been fabricated according to the invention. As may be seen in FIG. 3, contoured surface 56 includes a fabric cover 54 in which a plurality of depressions 60 have been formed. Depressions 60 conform to the projections 50 in the contoured screen 40 which is illustrated in FIG. 2. A moisture barrier 58 is secured to cover 54 with a suitable adhesive to complete the fabrication of absorbent product 52.

Figure 4:
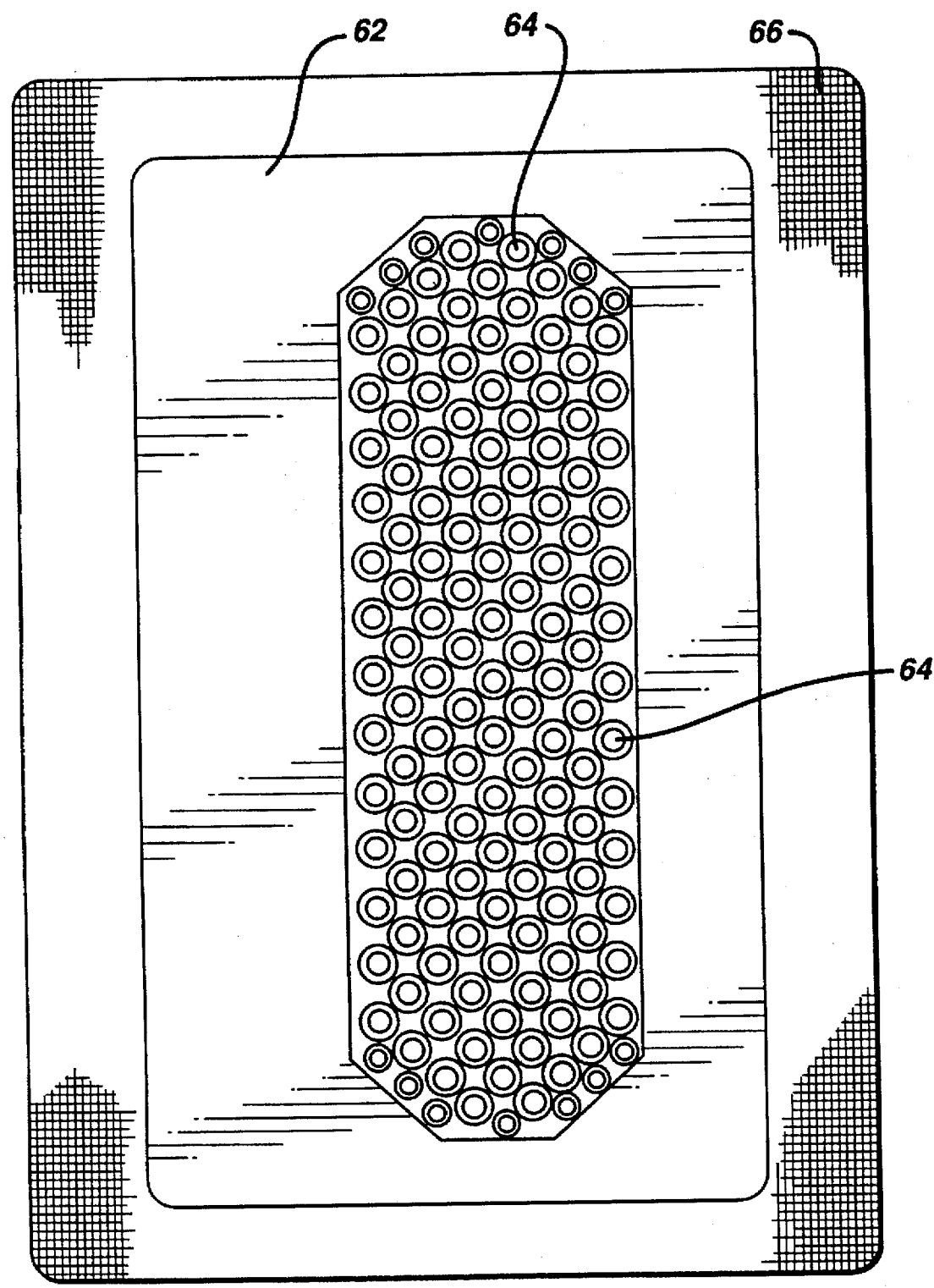
FIG. 4 is a plan view of an insert and a flat screen which is used according to a second embodiment of the invention.

According to a second embodiment of the invention, depicted in FIG. 4, a molded insert 62 having a contoured surface, in this case including holes 64, may be used in conjunction with a flat screen 66 in lieu of the contoured screen 40 in the embodiment depicted in FIGS. 1 and 2. Insert 62 may in some cases be more economical to manufacture than the contoured screen 40, although contoured screen 40 permits better air flow through the shaping assembly 12 during manufacturing of the three-dimensional fabric according to the invention.

Figure 5:
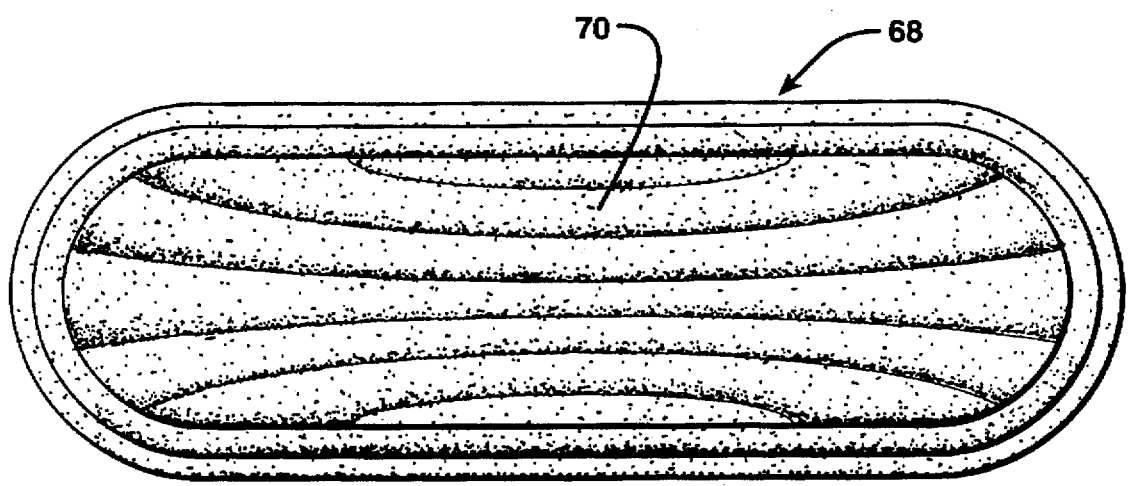
FIG. 5 is a plan view an absorbent product fabricated according to the invention which has an alternative contoured surface configuration.

As shown in FIG. 5, an absorbent product 68 can, by varying the shape of the contoured screen 40 or molded insert 62, be formed in substantially any desired shape. In this case, absorbent product 68 has a contoured surface 70 having a pattern of substantially longitudinal ribs and fluid-transporting valleys. For example, different contours may improve fluid transport, reduce fluid run off, minimize the contact surface of the fabric to a wound or vaginal wall to reduce removal forces, or be shaped so as better conform to the anatomy of the consumer or patient.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. An apparatus for manufacturing a three-dimensional fabric material which may be used in absorbent garments or dressings, comprising:

an apertured collector element having a predetermined three-dimensional shape;

means for positioning fabric material which contains a thermobondable component adjacent to one side of said apertured collector element;

means for developing a pressure differential between said one side of said apertured collector element and a second, opposite side to force said fabric material against said one side of said apertured collector element so that said fabric material conforms to said predetermined three-dimensional shape; and means for heating said so-conformed fabric material to melt the thermobondable component and then cooling to solidify the fabric material into said three-dimensional shape.

2. An apparatus according to claim 1, wherein said apertured collector element comprises a screen which is contoured into said three-dimensional shape.

3. An apparatus according to claim 1, wherein said apertured collector element comprises a molded insert.

4. An apparatus for manufacturing a three-dimensional fabric which may be used in absorbent garments or dressings, comprising:

an apertured collector element having a predetermined three-dimensional shape;

means for positioning a web of fabric material containing a thermobondable component adjacent to one side of said apertured collector element;

means for positioning fibrous fill material adjacent to said web of fabric material; and means for heating said web fabric material and said fibrous fill material to melt the thermobondable component and then cooling to solidify the fabric material into said three-dimensional shape.

5. An apparatus according to claim 4, wherein said apertured collector element comprises a screen which is contoured into said three-dimensional shape.

6. An apparatus according to claim 4, wherein said apertured collector element comprises a molded insert.

* * * * *